(12) United States Patent
Pierson et al.

(10) Patent No.: US 8,237,011 B2
(45) Date of Patent: Aug. 7, 2012

(54) COATING COMPOSITIONS AND COATED SUBSTRATES FOR ARTICLES OF MANUFACTURE USED IN CONTACT WITH HUMAN BODY SURFACES

(75) Inventors: Linda M. Pierson, Flemington, NJ (US); Susan K. Brown-Skrobot, Hillsborough, NJ (US); Ching-Yun M. Yang, Princeton Junction, NJ (US)

(73) Assignee: McNeil—PPC, Inc., Skillman, NJ (US)

( * ) Notice: Subject to any disclaimer, the term of this patent is extended or adjusted under 35 U.S.C. 154(b) by 380 days.

(21) Appl. No.: 12/621,681

(22) Filed: Nov. 19, 2009

(65) Prior Publication Data

US 2010/0130951 A1 May 27, 2010

Related U.S. Application Data

(60) Provisional application No. 61/116,785, filed on Nov. 21, 2008.

(51) Int. Cl.
*A61F 13/15* (2006.01)
*A61F 13/20* (2006.01)

(52) U.S. Cl. ........ 604/367; 604/370; 604/372; 604/381; 604/382; 604/385.17

(58) Field of Classification Search .................. 604/367, 604/370, 372, 381, 382, 385.17
See application file for complete search history.

(56) References Cited

U.S. PATENT DOCUMENTS

| | | |
|---|---|---|
| 3,796,219 A | 3/1974 | Hanke |
| 4,294,253 A | 10/1981 | Friese |
| 4,438,167 A | 3/1984 | Schwarz |
| 4,582,717 A | 4/1986 | von Bittera et al. |
| 4,642,108 A | 2/1987 | Sustmann |
| 5,295,984 A | 3/1994 | Contente et al. |
| 5,389,374 A | 2/1995 | Brown-Skrobot |
| 5,466,685 A | 11/1995 | Brown-Skrobot et al. |
| 5,547,985 A | 8/1996 | Brown-Skrobot et al. |
| 5,633,245 A | 5/1997 | Brown-Skrobot et al. |
| 5,641,503 A | 6/1997 | Brown-Skrobot |
| 5,679,369 A | 10/1997 | Brown-Skrobot |
| 5,705,182 A | 1/1998 | Brown-Skrobot |
| 5,753,252 A | 5/1998 | Brown-Skrobot |
| 5,832,576 A | 11/1998 | Leutwyler et al. |
| 6,096,332 A * | 8/2000 | Yang ............................ 424/431 |
| 6,310,269 B1 | 10/2001 | Friese et al. |
| 6,316,019 B1 | 11/2001 | Yang |
| 6,537,414 B1 | 3/2003 | Schoelling |
| 6,570,055 B2 | 5/2003 | Yang et al. |
| 6,748,634 B2 | 6/2004 | Nguyen et al. |
| 2002/0143305 A1 | 10/2002 | Yang et al. |
| 2002/0151859 A1 | 10/2002 | Schoelling |

OTHER PUBLICATIONS

European Pharmacopoeia, Fifth Edition, vol. 2, Published in accordance with the Convention on the Elaboration of a European Pharmacopoeia (European Treaty Series No. 50), 2004, ISBN: 92-871-5281-0, "Viscose Wadding, Absorbent" 01/2005:0217, p. 2681-2682.

Reiser et al., "Production of Toxic Shock Syndrome Toxin 1 by *Staphylococcus aureus* Restricted to Endogenous Air in Tampons", *Journal of Clinical Microbiology*, vol. 25, No. 8, Aug. 1987, p. 1450-1452.

* cited by examiner

*Primary Examiner* — Jacqueline F. Stephens

(57) ABSTRACT

A composition of matter includes a flexible substrate and a coating disposed on the substrate. The coating comprises about 10-60 wt-% of a waxy compound and about 90-40 wt-% of a diluent. The coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

16 Claims, No Drawings

COATING COMPOSITIONS AND COATED SUBSTRATES FOR ARTICLES OF MANUFACTURE USED IN CONTACT WITH HUMAN BODY SURFACES

CROSS-REFERENCE TO RELATED APPLICATIONS

This application claims the benefit of U.S. provisional application 61/116,785 filed on Nov. 21, 2008, the complete disclosure of which is hereby incorporated herein by reference for all purposes.

This application relates to U.S. application Ser. No. 12/621,678, entitled "Chiller Box" filed on even date herewith.

BACKGROUND OF THE INVENTION

The present invention relates to coating compositions for flexible, sheet-like substrates, coated flexible, sheet-like substrates for articles of manufacture used in contact with human body surfaces, and a process for adding waxy compositions to flexible, sheet-like substrates. The present invention is particularly useful for coating compositions for flexible, sheet-like substrates, coated flexible, sheet-like substrates used in the manufacture of disposable absorbent articles, specifically suited for coated flexible, sheet-like substrates used in the manufacture of tampons.

There are several methods of delivering waxy compositions to their intended targets, including but not limited to oral, topical, and transdermal methods. Disposable absorbent articles can be used as vehicles for topical delivery to the vaginal canal, perineum, and related areas, as well as for treatment sites for the discharged fluids to come in contact with the waxy compositions, as they are captured by the product.

Duchane, U.S. Pat. No. 3,796,219 discloses a water-soluble, thermoplastic compound for hygienic and medical applications, such as for use as an insertion aid coating for tampons and as the matrix structure for suppositories. The coating is stable in temperatures up to 65° C., and it provides lubricity at temperatures below 65° C. when exposed to shear forces, as those present during insertion of the tampon. Duchane discloses the use of two olefinic diols, polyethylene glycol and propylene glycol in combination with hydroxypropyl cellulose (HPC) having a molecular weight of approximately 75,000. The resulting composition is stable at temperatures up to 65° C. Von Bittera et al., U.S. Pat. No. 4,582,717, discloses a process for producing vaginal tampons containing a pharmaceutical active compound. The process involves preparing a material containing the active compound and additional formulation auxiliaries, heating the material to a temperature in excess of 40° C., cooling the melt to 40° C., and then injecting the cooled material into pre-warmed tampons. One of the formulation auxiliaries disclosed in von Bittera is polyethylene glycol (PEG) having moderate molecular weight.

Yang, U.S. Pat. No. 6,316,019 discloses a process for making a tampon including the application to a substrate of a solution containing a pharmaceutically active compound. The solution is liquid at a temperature of less than about 35° C., and it is applied to the disposable absorbent article at a temperature of less than 40° C.

A common theme of the art shown above is the attempt to provide a coating that is stable above room temperature, but is liquid at or near body temperature (37° C.). This provides significant challenges to handling the components in high speed manufacturing processes without loss by transfer to the processing equipment.

Brown-Skrobot, U.S. Pat. No. 5,679,369, discloses additives to tampons to inhibit the production of toxic shock syndrome toxin-1. The additives generally are not liquid at or near room temperature, and therefore, they require a carrier material, such as isopropyl alcohol. This technology represents an important advance in the art, but the disclosed process of applying the additive may require a recovery process to capture the volatile alcohol.

While this is an advance in the art, the ability to add substantial amounts of the pharmaceutically active compound to the substrate to form a robust and flexible coated material is limited.

Therefore, what is needed are coating compositions and coated substrates that form a robust and flexible coated material and that provide desired properties to articles of manufacture used in contact with human body surfaces, such as a body-side liner or cover of an absorbent article, such as a tampon. Further, what is needed are coating compositions and coated substrates that are processable in a commercially efficient manner, that provide satisfactory fluid transport into the absorbent article, and that aid in removal of the tampon from an overwrapper or applicator prior to and/or during use.

SUMMARY OF THE INVENTION

We have found coating compositions and coated substrates that form a robust and flexible coated material and that provide desired properties to articles of manufacture used in contact with human body surfaces, such as a body-side liner or cover of an absorbent article, such as a tampon.

We have found that such coating compositions and coated substrates are processable in a commercially efficient manner, and that they provide satisfactory fluid transport into the absorbent article, and that they aid in removal of the tampon from an overwrapper or applicator prior to and/or during use.

In one embodiment of the invention, a composition of matter includes a flexible substrate and a coating disposed on the substrate. The coating comprises about 10-60 wt-% of a waxy compound and about 90-40 wt-% of a diluent. The waxy compound is selected from the group consisting of A) monoesters of a polyhydric aliphatic alcohol and a fatty acid containing from eight to eighteen carbon atoms and wherein said monoester has at least one hydroxyl group associated with its aliphatic alcohol residue; B) diesters of a polyhydric aliphatic alcohol and a fatty acid containing from eight to eighteen carbon atoms and wherein said diester has at least one hydroxyl group associated with its aliphatic alcohol residue; and C) mixtures of said monoesters and diesters. The coating forms a stable liquid mixture at a temperature between about 35° C. and about 100° C., has a liquefaction temperature of at least about 30° C., and has a contact angle with a flat surface of the substrate of less than about 35° when measured at a temperature of 60° C. In one preferred embodiment, the coating forms a stable liquid mixture at a temperature between about 40° C. and about 75° C. In another preferred embodiment, the liquid mixture has a liquefaction temperature of at least about 35° C. In another preferred embodiment, the diluent comprises a hydrophilic agent and a lyophilic agent.

In another embodiment of the invention, a coating composition includes about 10-60 wt-% of a waxy compound and about 90-40 wt-% of a diluent. The waxy compound is selected from the group consisting of A) monoesters of a polyhydric aliphatic alcohol and a fatty acid containing from eight to eighteen carbon atoms and wherein said monoester has at least one hydroxyl group associated with its aliphatic alcohol residue; B) diesters of a polyhydric aliphatic alcohol and a fatty acid containing from eight to eighteen carbon atoms and wherein said diester has at least one hydroxyl group associated with its aliphatic alcohol residue; and C) mixtures of said monoesters and diesters. The coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

In another embodiment of the invention, an intravaginal device includes an insertable element that is substantially enclosed within a cover material. The cover material includes a flexible substrate and a coating disposed on the substrate. The coating includes about 10-60 wt-% of a waxy compound and about 90-40 wt-% of a diluent. The waxy compound is selected from the group consisting of A) monoesters of a polyhydric aliphatic alcohol and a fatty acid containing from eight to eighteen carbon atoms and wherein said monoester has at least one hydroxyl group associated with its aliphatic alcohol residue; B) diesters of a polyhydric aliphatic alcohol and a fatty acid containing from eight to eighteen carbon atoms and wherein said diester has at least one hydroxyl group associated with its aliphatic alcohol residue; and C) mixtures of said monoesters and diesters. The coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

DETAILED DESCRIPTION OF THE INVENTION

The present invention relates to a process for adding waxy components to substrates, specifically substrates used in the manufacture of disposable absorbent articles, to the articles during manufacture, or to the finished product. The process incorporates the use of a liquid solution to apply the waxy component to substrates.

The present invention also relates to a liquid coating composition comprising the waxy component and a diluent, which liquid composition forms a stable liquid mixture at a temperature between about 35° C. and about 100° C., has a liquefaction temperature of at least about 30° C., and has a contact angle with a flat surface of the substrate of less than about 35° when measured at a temperature of 60° C.

One advantage the present invention provides is that the coated substrate is surprisingly robust. We have found that the resulting coating neither flakes off of the substrate nor is significantly rubbed off of the substrate during processing. This permits economic, high-speed processing of the coated substrate to form an article of manufacture used in contact with human body surfaces.

As used in this specification and the appended claims, liquid is defined to be a substance that has a definite volume but no definite form except such as given by its container. A solution is defined herein to be a homogeneous mixture of a substance (solid, liquid, or gas) dissolved in a liquid, the solvent.

As used herein, the term "surfactant" refers to a surface active agent, i.e., one that modifies the nature of surfaces. Surfactants are often used as wetting agents, detergents, emulsifiers, dispersing agents, penetrants, and antifoaming agents. Surfactants may be anionic, cationic, nonionic and ampholytic. Preferably, the surfactant used in the present invention is a nonionic surfactant. Nonionic surfactants are generally less irritating of human body tissue, and they are therefore more acceptable in uses that contact such tissue.

As used herein, the term "hydrophilic agent" refers to a substance that readily associates with water, and the term "lyophilic agent" refers to an agent that attracts lipids in a colloid system, describing a colloidal system in which the dispersed phase is a lipids and attracts the dispersing medium. One measure of the relative hydrophilicity and lyophilicity of an agent is the HLB or hydrophile-lyophile balance with a high HLB reflecting a relatively hydrophilic agent and a low HLB reflecting a relatively lyophilic agent. Preferably the lyophilic agents have an HLB of less than about 10, more preferably, less than about 8, and most preferably, less than about 5.

The waxy compositions useful in the present invention used in the present invention are useful to inhibit the production of toxins by various bacteria as disclosed in Brown-Skrobot and Brown-Skrobot et al., U.S. Pat. Nos. 5,389,374; 5,547,985; 5,641,503; 5,679,369; and 5,705,182, all of which are incorporated by reference. These compositions are selected from the group consisting of: monoesters of a polyhydric aliphatic alcohol and a fatty acid containing from eight to eighteen carbon atoms and wherein said monoester has at least one hydroxyl group associated with its aliphatic alcohol residue; diesters of a polyhydric aliphatic alcohol and a fatty acid containing from eight to eighteen carbon atoms and wherein said diester has at least one hydroxyl group associated with its aliphatic alcohol residue; and mixtures of said monoesters and diesters. Preferably, the active composition is glycerol monolaurate.

The diluents of the present invention are compatible with both the waxy composition and the substrate to which the liquid composition will be applied. The diluent may be a single component or may be a multi-component system. A single component diluent may be selected based upon its compatibility with the waxy component. For example, employing GML as the waxy component (HLB of 5.2, one may select diluents with a similar HLB, preferably an HLB of 5.2+/− about 2. If it is desired to impart other properties (such as wettability by an aqueous liquid) by employing a diluent such as a hydrophilic olefinic diol, an additional diluent, such as a surfactant having an HLB similar to GML, e.g., about 3.2 to about 7.2, can be incorporated to form a two-component diluent.

The olefinic diols of the present invention are highly hydrophilic and/or very miscible with water. Thus, aqueous bodily fluids that may be absorbed by absorbent structures treated with the present solution will have a greater affinity for such structures than for structures treated with the waxy composition of the present invention in the absence of the olefinic diol.

A representative, non-limiting list of useful diols includes $C_{2-8}$ diols and polyglycols, and the like. Preferably, the diol is selected from the group consisting of glycols ($C_2$ and $C_3$ diols) and polyglycols. As used in the specification and the claims, the term "polyglycol" refers to a dihydroxy ether formed by dehydration of two or more glycol molecules. A representative, non-limiting list of useful polyglycols includes ethylene glycol, propylene glycol, polyethylene glycols, polypropylene glycols, methoxypolyethylene glycols, polybutylene glycols, or block copolymers of butylene oxide and ethylene oxide. Among the aforementioned polyglycols, polyethylene glycol having a molecular weight of less than about 600, and polypropylene glycol having a molecular weight of less than about 4,000, are preferred.

Other diluents or diluent components may include surfactants, such as fatty acid esters and ethoxylated sugar derivatives. Preferred fatty acid esters include sorbitan fatty acid esters. A representative, non-limiting list of useful sorbitan fatty acid esters includes sorbitan monooleate (HLB: 4.3), sorbitan monostearate (HLB: 4.7), sorbitan monopalmitate (HLB: 6.7), sorbitan monolaurate (HLB: 8.6), sorbitan tristearate (HLB: 2.1), and sorbitan trioleate (HLB: 1.8). Among the aforementioned sorbitan fatty acid esters, sorbitan monooleate is most preferred.

Preferred ethoxylated sugar derivatives include the class of methyl glucose derivatives. A representative, non-limiting list of useful methyl glucose derivatives includes methyl gluceth-10, methyl glucose-20, methyl glucose-20 distearate, methyl glucose dioleate (HLB: 5), and methyl glucose sesquistearate (HLB: 6), PEG-120 methyl glucose dioleate, and PEG-20 methyl glucose sesquistearate.

Other diluents or diluent components may include mono-, di-, or triglycerides that have an HLB value between about 3 and about 10, preferably between about 3 and about 7.5, including without limitation, caprylic/capric triglyceride (HLB of 5), available as NEOBEE®z® M-5 caprylic/capric triglyceride from Stephan Company Northfield, Ill., USA; oleic triglyceride (HLB of 7), available as FLORASUN™ 90 from International Flora Technologies, Ltd, Chandler, Ariz., USA.

Preferably, the liquid mixture includes about 10 to about 60 wt % of the waxy component and about 90 to about 40 wt-% of the diluent, more preferably about 20 to about 50 wt % of the waxy component and about 70 to about 50 wt-% of the diluent.

Diluent systems comprising hydrophilic and lyophilic diluent components may take the ranges shown below in Table 1:

TABLE 1

|  | Hydrophilic component(s) (wt-%) | Lyophilic component(s) (wt-%) |
|---|---|---|
| Useful | 0-100 | 100-0 |
| Preferred | 25-80 | 75-20 |
| More preferred | 40-75 | 60-25 |
| Most preferred | 50-70 | 50-30 |

An example of the preparation of the liquid composition of the present invention is described below with reference to a particular system comprising glycerol monolaurate as the waxy component and a multi-component diluent system. Other liquid compositions may be similarly prepared, whether there is more than one waxy component or whether there is only one diluent. Generally, the diluent or diluent system will be heated to a temperature at which the waxy component(s) will be liquefied in combination with the diluent. The mixture will be agitated to ensure sufficient component homogeneity, and the waxy component(s) will be added at a rate at which the liquid mixture can be maintained without solidification.

In one preferred embodiment, the liquid composition may be prepared by combining an olefinic diol and a surfactant agent while stirring and heating to about 60° C. to form the diluent. While continuing to stir, the waxy substance may be added to the diluent, and the heat maintained. In the example of glycerol monolaurate, PEG-400 and sorbitan monooleate (SPAN® 80), the glycerol monolaurate may be added at a rate that does not cause the temperature of the solution to drop below 52° C. We have found that this mixture starts to clear up at ~52° C. and completely clear at 55° C. Heating the solution to about 60° C. can substantially assure complete mixing of the coating composition.

After the solution is prepared, in accordance to the description above, it is then applied to a substrate. Useful substrates include, but are not limited to, films (e.g., apertured or non-apertured), fabrics (e.g., woven, knit, or non-woven), strings (e.g., threads, cords, tapes, and ribbons) and the like. Films may be relatively homogenous films or may be multilayered films formed by lamination, co-extrusion, and other film-forming methods. The films may be apertured to permit movement of fluids, such as gases, and more preferably liquids, through the film.

Fabric substrates may comprise absorbent and/or non-absorbent fibers, and the fibers may be homogeneous or multi-component. A representative, non-limiting list of useful fibers includes, without limitation, cellulose, rayon, nylon, acrylic, polyester, polyethylene, polypropylene, ethylene vinyl acetate, polyurethane, and the like. Multi-component fibers may be bicomponent or more and may have a sheath/core configuration, a side-by-side configuration, or other configuration that would be recognized by one of ordinary skill in the art.

A representative, non-limiting list of useful non-woven fabrics includes spunbonded fabric, thermal bonded fabric, resin bonded fabric, hydroentangled fabric, spun-lace fabric, meltblown fabric, needlepunched fabric, and the like; apertured and non-apertured films.

The coating composition may be applied to the flexible, sheet-like substrate in ways known to those of ordinary skill in the art. A representative, non-limiting list of useful application methods includes dip, immersion, roller-transfer, kiss-coating, spray, doctor blade, gravure, relief print, and the like.

In a preferred embodiment, the coated substrate is rapidly chilled to form a robust flexible material. Preferably, the coating composition remains adhered to the substrate when substrate is bent at a 180° angle over a rod having a diameter of less than about 5 mm and does not transfer significantly to a steel surface when pressed against the surface. This is indicative that the coated substrate will stand up to the rigors of further processing to produce an article of manufacture such as a disposable absorbent article.

The coated substrate may be chilled through the use of a chiller device comprising an enclosure having at least an inlet to receive the coated substrate, an outlet to discharge the coated substrate, and means to cool the coated substrate and to maintain the temperature in the enclosure at a temperature of less than about 0° C., more preferably to less than about −20° C., as described in U.S. application Ser. No. 12/621,678, entitled "Chiller Box" filed on even date herewith.

The amount of pharmaceutically active compound applied to a substrate, useful in the present invention, is up to about 4 wt-%, preferably from about 0.1 to about 4 weight percent; more preferably, from about 0.5 to about 3 weight percent; and most preferably, from about 0.9 to about 2.5 weight percent. The amount of liquid mixture applied to the substrate, determined from the preferred solution ratios and amount of pharmaceutically active compound, is up to about 10 wt-%, preferably from about 0.2 to about 8 weight percent; more preferably, from about 1 to about 6 weight percent; and most preferably, from about 3 to about 5 weight percent.

The substrates of the present invention can be used independently, or as an element in the manufacture of disposable articles. Such articles can include patches for topical or transdermal applications, nasal pads (nasal tampons), diapers, incontinence products, sanitary protection products, body wipes, bedsheets and surgical gowns. Preferably, the substrates are elements used in the manufacture of sanitary protection and incontinence products. The solutions can also be applied to finished disposable articles.

Typically, sanitary protection articles fall into two distinct categories, those worn externally in contact with the perineum, and those worn internally, partially or wholly contained within the vaginal canal. External sanitary protection products include, without limitation, pantiliners, full-size pads, and ultrathins.

Internal sanitary protection products can be defined as absorbing products, such as tampons, and the like; collecting products, such as described in Contente et al., U.S. Pat. No. 5,295,984 and the like; or a combination of the two. U.S. Pat. Nos. 4,294,253 and 4,642,108, incorporated by reference herein, disclose tampon constructions and processes of manufacture. A preferred disposable absorbent article of the present invention, for the solution to be applied to, is a sanitary tampon. Other internal products can include incontinence articles, such as pessaries and other urinary tract support devices.

A process for producing disposable absorbent articles comprises encasing at least a portion of an absorbent material with a liquid permeable material, wherein the discharged fluids, contact and penetrate the liquid permeable material, and are drawn into the absorbent material for storage. In a preferred embodiment, the liquid permeable material is the coated substrate of the present invention.

A representative, non-limiting list of materials useful as the absorbent material includes cellulosic fibers, such as wood pulp and cotton pulp; synthetic fibers, such as polyesters and polyolefins; superabsorbent polymers, such as sodium polyacrylate, and the like.

Optionally, the process can further comprise encasing a second portion of the absorbent material with a liquid impermeable material, to prevent the collected fluid from transferring completely through the article. Useful liquid impermeable materials include, without limitation, polymeric films or coatings, such as polyolefins (e.g., polyethylene and polypropylene), polyvinyls (e.g., polyvinyl acetate, polyvinyl chloride, and polyvinylidene chloride), copolymers (e.g., ethylene vinyl acetate), and blends or laminates of one or more of the above polymers; bodily fluid repellant structures such as nonwovens, apertured films, and repellant fiber layers integrated into the bottom layer of the absorbent materials.

Test Methods:
  Contact Angle

The contact angle (θ) is the angle at which a liquid/vapor interface meets the solid surface. The contact angle is specific for any given system and is determined by the interactions across the three interfaces, LV, SV, and SL. The subscripts S, L, and V, stand for solid, liquid, and vapor, respectively. Most often the concept is illustrated with a small liquid droplet resting on a flat horizontal solid surface using a goniometer. The contact angle is controlled by three forces: $\gamma_{LV}$ (liquid vapor surface tension), $\gamma_{SV}$ (solid vapor surface tension), and $\gamma_{SL}$ (solid-liquid interfacial tension). A balance of the three relation leads to Young's equation: $\gamma_{SV} = \gamma_{SL} + \gamma_{LV} \cos \theta$.

The contact angles in this disclosure were measured using a DSA 100 instrument (Krüss GmbH, Hamburg, Germany). Since contact angles have to be measured in molten/liquid stage, the formulations analyzed were all placed into an oven at 60° C. and allowed to equilibrate, unless otherwise noted. The test surfaces were created by adhering a polymer film formed of a blend of low density polyethylene, linear low density polyethylene, and high density polyethylene onto a glass substrate using double-sided tape on its sides to keep it flat. The surfaces were then placed into the sample chamber of the instrument, which was also temperature regulated at 60° C. (unless otherwise noted) by a temperature-controlled water bath. The samples were loaded into syringes and dispensed from a needle on to the surfaces with an approximate diameter of 0.5 mm. Drops are created and increased in size until they freely fall from the needle onto the surface. An image is captured of the drop on the surface when equilibrium is reached.

The contact angles are calculated by analyzing the images captured using the Drop Shape Analysis (DSA) for Windows™ ver. 1.90.0.14 software package (Krüss GmbH, Hamburg, Germany). All of the contact angles were determined using the same fitting method to avoid variation due to the fitting method. The first step is to determine the baseline, i.e. where the drop meets the surface. This can be done automatically in the software, but can be manually adjusted by one-skilled in the art. The fitting method chosen was the circular segment method (circle fitting). The drop outline is adapted mathematically to a circular segment shape. In this way the whole drop outline can be evaluated and not just the area of intersection with the baseline.

When the spreading process comes to an end and an equilibrium state is reached, this state is characterized by the contact angle (θ).

Mounting the surfaces down with an adhesive helped to control any wrinkling of the film during heat up and equilibration of the surface to the desired temperature.

Differential Scanning Calorimetry

DSC (Differential Scanning Calorimetry) is a thermo analytical method. It measures the difference in the amount of heat required to increase the temperature of a sample and reference. A DSC (TA Instruments Model Q 200, with Universal Analysis 200 software V4.4A, Aluminum sample pans with hermetic lids) is used to study the phase transition from solid to liquid of a formulation. A formulation in liquid state is added to a pre-weighed aluminum DSC sample pan. The final sample weight was recorded and the sample pan sealed with a hermetic lid. Sample weights are in the range of 6 to 10 millgrams.

The DSC measurement for each sample is run a heat/cool/heat series. The sample starts out at 25° C. and heat is increased at a constant rate of 10 degree/min to a max of 80° C. The sample is then cooled to −20° C., and reheated to 80° C. with both cooling and heating rate of 10°/min. The liquifaction temperature is defined and measured as the maximum of the first heat cycle or the first peak of the DSC chart.

EXAMPLES

Example 1

In order to determine whether the coatings of the present invention are suitable for commercial production of tampons, tampons were produced in accordance with the general teaching of Friese et al., U.S. Pat. No. 6,310,269; Leutwyler et al., U.S. Pat. No. 5,832,576; PPC708; and Schoelling US Pat. App. No. 2002/0151859 employing the apertured film cover, generally as disclosed in U.S. Pat. No. 6,537,414; the disclosures of which are herein incorporated by reference.

A batch of coating formulation was prepared as follows:
1. Add 25 parts by weight of PEG-400 and 25 parts by weight of SPAN 80. Heat it to 60° C. with stirring.
2. While stirring, slowly, add 50 parts by weight of GML. When GML is added, the temperature starts to drop. Keep on heating and stirring. Add GML at a rate such that the solution stays above 52° C. The mixture starts to clear up at ~52° C. and completely clear at 55° C. It is suggested to heat the solution to 60° C. to assure the completion of GML/PEG/SPAN mixing.

The coating was applied to the apertured film cover material off-line prior to slitting and rolling to form an apertured film cover supply. The supply (having a target amount of about 2 mg GML per tampon) was unwound on commercial processing equipment to form the tampons generally as described above. After manufacture of the tampons, the amount of GML remaining on the cover was determined by HPLC with an Evaporative Light Scattering Detector.

The results are shown below in Table 2.

TABLE 2

|  | o.b. ® Normal Absorbency Tampons (Germany) | o.b. ® Super Absorbency Tampons (Germany) |
|---|---|---|
| Mean of 6 tampons | 2.25 mg/tampon | 2.11 mg/tampon |
| Composite of 10 isolated covers | 2.06 mg/tampon | 1.94 mg/tampon |
| Calculate from GML on raw film/tampon | 2.07 mg/tampon | 2.07 mg/tampon |

The analytical data reported above shows there is no significant loss from raw film to finished tampons.

Example 2

A series of coating compositions was prepared, generally as follows:
1. Add desired amount of diluent to a mixing vessel and heat to 60° C. while stirring.
2. While stirring, slowly, add desired amount of waxy composition, e.g., GML. As the addition of the waxy composition tends to lower the temperature of the mixture, continue to heat and stir. Heat to a temperature until the mixture turns clear, an indication of a true solution. This is under 60° C.

The mixtures were then assessed to determine their liquefaction point (the first solid-to-liquid heat absorption peak determined via Differential Scanning Calorimetry) and their Contact Angle with a selected substrate at 60° C. The results are shown in Table 3, below.

TABLE 3

| Formulation | Component Wt-% | Ratio of Hydrophilic/ lyophilic diluents | DSC MP ° C. | Contact Angle @60° C. |
|---|---|---|---|---|
| GML/PEG 400/ SPAN ® 80 | 32/34/34 | 50/50 | 41 | |
| GML/1,2-propanediol/ SPAN ® 80 | 32/34/34 | 50/50 | 34 | |
| GML/1,2-propanediol/ SPAN ® 80 | 50/25/25 | 50/50 | 40 | 15.2 |
| GML/1,2-propanediol/ SPAN ® 80 | 55/18/27 | 40/60 | 44 | |
| GML/1,3-propanediol/ SPAN ® 80 | 50/25/25 | 50/50 | 43 | 9.4 |
| GML/PEG 400/ SPAN ® 80 | 50/25/25 | 50/50 | 49 | |
| GML/PEG 400/ SPAN 80 ™ | 50/35/15 | 70/30 | 47 | 25.5 |
| Glycerol monostearate/ PEG 400/ SPAN ® 80 | 50/25/25 | 50/50 | 47 | 15.9* |
| GML/PEG 400/ | 50/25/25 | 50/50 | 50 | 11.6 |

TABLE 3-continued

| Formulation | Component Wt-% | Ratio of Hydrophilic/ lyophilic diluents | DSC MP ° C. | Contact Angle @60° C. |
|---|---|---|---|---|
| Neobee ® 80 M-5 GML/PEG 400/ Florasun ™ 90 | 50/25/25 | 50/50 | 51.5 | 12 |
| GML | 100 | — | 59 | 9* |
| GML/PEG 400 | 50/50 | 100/100 | 49 | 29.1 |
| GML/PEG 400 | 40/60 | 100/0 | 43 | 34.8 |
| GML/PEG 400 | 30/70 | 100/0 | 41 | 40.6 |
| GML/PEG 400 | 20/80 | 100/0 | 40 | 44.3 |
| GML/Neobee ® M-5 ™ | 50/50 | 100/0 | 54.9 | 12.5 |
| Water | 100 | — | — | 87.1 |
| PEG 400 | 100 | — | — | 60.7 |

*Formulation T was raised to 70° C.
DSC MP was measured from the first solid to liquid heat absorption peak.
Contact Angle is the contact angle of a formulation at 60° C. on a flat PE film placing on a 60° C. surface
SPAN ® 80 is sorbitan monooleate with HLB value of 4.3
Neobee ® M-5 is a caprylic triglyceride with HLB value of 5
Florasun ™ 90 is an oleic triglyceride with HLB value of 7

The invention has been illustrated by, but is not intended to be limited to, the above description and examples. The scope of the invention is to be determined by the claims attached hereto.

What is claimed is:

1. A composition of matter comprising:
   a) a flexible substrate;
   b) a coating disposed on the substrate, wherein the coating comprises:
      i) about 10-60 wt-% of a waxy compound selected from the group consisting of:
         A) monoesters of a polyhydric aliphatic alcohol and a fatty acid containing from eight to eighteen carbon atoms and wherein said monoester has at least one hydroxyl group associated with its aliphatic alcohol residue;
         B) diesters of a polyhydric aliphatic alcohol and a fatty acid containing from eight to eighteen carbon atoms and wherein said diester has at least one hydroxyl group associated with its aliphatic alcohol residue; and
         C) mixtures of said monoesters and diesters; and
      ii) about 90-40 wt-% of a diluent;
   wherein the coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

2. The composition of claim 1, wherein the coating forms a stable liquid mixture at a temperature between about 40° C. and about 75° C.

3. The composition of claim 1, wherein the liquid mixture has a liquefaction temperature of at least about 35° C.

4. The composition of claim 1, wherein the diluent comprises a hydrophilic agent and a lyophilic agent.

5. The composition of claim 4, wherein the hydrophilic agent comprises an olefinic diol.

6. The composition of claim 1, wherein the coating has a contact angle with a flat surface of the substrate of less than 29.1° when measured at a temperature of 60° C.

7. A coating composition comprising:
   a) about 10-60 wt-% of a waxy compound selected from the group consisting of:

i) monoesters of a polyhydric aliphatic alcohol and a fatty acid containing from eight to eighteen carbon atoms and wherein said monoester has at least one hydroxyl group associated with its aliphatic alcohol residue;
ii) diesters of a polyhydric aliphatic alcohol and a fatty acid containing from eight to eighteen carbon atoms and wherein said diester has at least one hydroxyl group associated with its aliphatic alcohol residue; and
iii) mixtures of said monoesters and diesters; and
b) about 90-40 wt-% of a diluent;
wherein the diluent comprises a hydrophilic agent and a lyophilic agent and the coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

8. An intravaginal device comprising:
a) an insertable element;
b) substantially enclosed within a cover material comprising:
   i) a flexible substrate;
   ii) a coating disposed on the substrate, wherein the coating comprises a composition comprising:
      A) about 10-60 wt-% of a waxy compound selected from the group consisting of:
         1) monoesters of a polyhydric aliphatic alcohol and a fatty acid containing from eight to eighteen carbon atoms and wherein said monoester has at least one hydroxyl group associated with its aliphatic alcohol residue;
         2) diesters of a polyhydric aliphatic alcohol and a fatty acid containing from eight to eighteen carbon atoms and wherein said diester has at least one hydroxyl group associated with its aliphatic alcohol residue; and
         3) mixtures of said monoesters and diesters; and
      B) about 90-40 wt-% of a diluent;
   wherein the coating forms a stable liquid mixture at a temperature between about 35° C. and about 100° C., has a liquefaction temperature of at least about 30° C., and has a contact angle with a flat surface of the substrate of less than about 35° when measured at a temperature of 60° C.

9. The intravaginal device of claim 8, wherein the coating forms a stable liquid mixture at a temperature between about 40° C. and about 75° C.

10. The intravaginal device of claim 8, wherein the liquid mixture has a liquefaction temperature of at least about 35° C.

11. The intravaginal device of claim 8, wherein the diluent comprises a hydrophilic agent and a lyophilic agent.

12. The intravaginal device of claim 11, wherein the hydrophilic agent comprises an olefinic diol.

13. The intravaginal device of claim 8, wherein the flexible substrate comprises a film.

14. The intravaginal device of claim 13, wherein the film comprises an apertured film.

15. The intravaginal device of claim 8, wherein the flexible substrate comprises a nonwoven fabric.

16. The intravaginal device of claim 8, wherein the coating has a contact angle with a flat surface of the substrate of less than 29.1° when measured at a temperature of 60° C.

* * * * *